(12) United States Patent
Shukla et al.

(10) Patent No.: US 7,649,199 B2
(45) Date of Patent: *Jan. 19, 2010

(54) N-TYPE SEMICONDUCTOR MATERIALS IN THIN FILM TRANSISTORS AND ELECTRONIC DEVICES

(75) Inventors: Deepak Shukla, Webster, NY (US); Thomas R. Welter, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/101,179

(22) Filed: Apr. 11, 2008

(65) Prior Publication Data

US 2009/0256137 A1 Oct. 15, 2009

(51) Int. Cl.
*H01L 51/00* (2006.01)
*C07D 471/02* (2006.01)
(52) U.S. Cl. .................. 257/40; 546/66; 428/473.5
(58) Field of Classification Search ............... 546/66; 257/40; 428/473.5
See application file for complete search history.

(56) References Cited

U.S. PATENT DOCUMENTS

| | | | |
|---|---|---|---|
| 5,347,144 A | 9/1994 | Garnier et al. | |
| 6,387,727 B1 | 5/2002 | Katz et al. | |
| 2002/0164835 A1 | 11/2002 | Dimitrakopoulos et al. | |
| 2005/0176970 A1 | 8/2005 | Marks et al. | |
| 2006/0131564 A1 | 6/2006 | Shukla et al. | |
| 2006/0134823 A1 | 6/2006 | Shukla et al. | |
| 2006/0237712 A1 | 10/2006 | Shukla et al. | |
| 2007/0096084 A1 | 5/2007 | Shukla et al. | |
| 2007/0116895 A1 | 5/2007 | Shukla et al. | |

FOREIGN PATENT DOCUMENTS

| | | |
|---|---|---|
| EP | 1 041 653 | 10/2000 |
| JP | 2006045165 | 2/2006 |
| JP | 2006045165 A | 2/2006 |
| WO | WO 2007/061614 A1 | 5/2007 |
| WO | WO 2008/057610 A2 | 5/2008 |

OTHER PUBLICATIONS

U.S. Appl. No. 11/567,954, filed Dec. 7, 2006 titled Configurationally Controlled N,N'-Dicycloalkyl-Substituted Naphthalene-Based Tetracarboxylic Diimide Compounds As N-Type Semiconductor Materials for Thin Film Transistors, by Shukla et al.

*Primary Examiner*—Charanjit S Aulakh
(74) *Attorney, Agent, or Firm*—J. Lanny Tucker

(57) ABSTRACT

A thin film transistor comprises a layer of organic semiconductor that comprises an N,N'-1,4,5,8-naphthalenetetracarboxylic acid diimide having at least one cycloalkyl group having a fluorinated substituent at its 4-position that adopts an equatorial orientation in the trans configuration of the cycloalkyl group and an axial orientation in the cis configuration of the cycloalkyl group. Such transistors can be a field effect transistor having a dielectric layer, a gate electrode, a source electrode and a drain electrode. The gate electrode and the thin film of organic semiconductor material both contact the dielectric layer, and the source electrode and the drain electrode both contact the thin film of organic semiconductor material.

18 Claims, 1 Drawing Sheet

N-TYPE SEMICONDUCTOR MATERIALS IN THIN FILM TRANSISTORS AND ELECTRONIC DEVICES

FIELD OF THE INVENTION

The present invention relates to the use of N,N'-1,4,5,8-naphthalenetetracarboxylic acid diimides having a fluorinated cycloalkyl substituent as semiconductor materials in n-channel semiconductor films for thin film transistors. The invention also relates to the use of these materials in thin film transistors for electronic devices and methods of making such transistors and devices.

BACKGROUND OF THE INVENTION

Thin film transistors (TFT's) are widely used as switching elements in electronics, for example, in active-matrix liquid-crystal displays, smart cards, and a variety of other electronic devices and components thereof. The thin film transistor (TFT) is an example of a field effect transistor (FET). The best-known example of an FET is the MOSFET (Metal-Oxide-Semiconductor-FET), today's conventional switching element for high-speed applications. Presently, most thin film devices are made using amorphous silicon as the semiconductor. Amorphous silicon is a less expensive alternative to crystalline silicon. This fact is especially important for reducing the cost of transistors in large-area applications. Application of amorphous silicon is limited to relatively low speed devices, however, since its maximum mobility (0.5-1.0 $cm^2/V$ sec) is about a thousand times smaller than that of crystalline silicon.

Although amorphous silicon is less expensive than highly crystalline silicon for use in TFT's, amorphous silicon still has its drawbacks. The deposition of amorphous silicon, during the manufacture of transistors, requires relatively costly processes, such as plasma enhanced chemical vapor deposition and high temperatures (about 360° C.) to achieve the electrical characteristics sufficient for display applications. Such high processing temperatures disallow the use of substrates for deposition that are made of certain plastics that might otherwise be desirable for use in applications such as flexible displays.

In the past decade, organic materials have received attention as a potential alternative to inorganic materials such as amorphous silicon for use in semiconductor channels of TFT's. Organic semiconductor materials are simpler to process, especially those that are soluble in organic solvents and, therefore, capable of being applied to large areas by far less expensive processes, such as spin coating, dip coating and microcontact printing. Furthermore, organic materials may be deposited at lower temperatures, opening up a wider range of substrate materials, including plastics, for flexible electronic devices. Accordingly, thin film transistors made of organic materials can be viewed as a potential key technology for plastic circuitry in display drivers, portable computers, pagers, memory elements in transaction cards, and identification tags, where ease of fabrication, mechanical flexibility, and/or moderate operating temperatures are important considerations. Organic materials for use in semiconductor channels in TFT's are disclosed, for example, in U.S. Pat. No. 5,347,144 (Garnier et al.).

Considerable efforts have been made to discover new organic semiconductor materials that can be used in TFT's to provide the switching or logic elements in electronic components, many of which require significant mobilities, well above 0.01 $cm^2/Vs$, and current on/off ratios (hereinafter referred to as "on/off ratios") greater than 1000. Organic TFT's having such properties are potentially capable of use for electronic applications such as pixel drivers for displays and identification tags. Most of the compounds exhibiting these desirable properties are "p-type" or "p-channel," however, meaning that negative gate voltages, relative to the source voltage, are applied to induce positive charges (holes) in the channel region of the device.

As an alternative to p-type organic semiconductor materials, n-type organic semiconductor materials can be used in TFT's as an alternative to p-type organic semiconductor materials, where the terminology "n-type" or "n-channel" indicates that positive gate voltages, relative to the source voltage, are applied to induce negative charges in the channel region of the device.

Moreover, one important type of TFT circuit, known as a complementary circuit, requires an n-type semiconductor material in addition to a p-type semiconductor material (see Dodabalapur et al. *Appl. Phys. Lett.* 1996, 69, 4227). In particular, the fabrication of complementary circuits requires at least one p-channel TFT and at least one n-channel TFT. Simple components such as inverters have been realized using complementary circuit architecture. Advantages of complementary circuits, relative to ordinary TFT circuits, include lower power dissipation, longer lifetime, and better tolerance of noise. In such complementary circuits, it is often desirable to have the mobility and the on/off ratio of an n-channel device similar in magnitude to the mobility and the on/off ratio of a p-channel device. Hybrid complementary circuits using an organic p-type semiconductor and an inorganic n-type semiconductor are known, as described by Dodabalapur et al. (*Appl. Phys. Lett.* 1996, 68, 2264.), but for ease of fabrication, an organic n-channel semiconductor material would be desired in such circuits.

Only a limited number of organic materials have been developed for use as a semiconductor n-channel in TFT's. One such material, buckminsterfullerene C60, exhibits a mobility of 0.08 $cm^2/Vs$ but is considered unstable in air. Perfluorinated copper phthalocyanine has a mobility of 0.03 $cm^2/Vs$, and is generally stable to air operation, but substrates must be heated to temperatures above 100° C. in order to maximize the mobility in this material. Other n-channel semiconductors, including some based on a naphthalene framework, are known but have lower mobilities. One such naphthalene-based n-channel semiconductor material, tetracyanonaphthoquino-dimethane (TCNNQD), is capable of operation in air, but the material has displayed a low on/off ratio and is also difficult to prepare and purify.

U.S. Patent Application Publication 2002/0164835 A1 (Dimitrakopoulos et al.) discloses improved n-channel semiconductor films made of perylene tetracarboxylic acid diimide compounds, as compared to naphthalene-based compounds, one example of which is N,N'-di(n-1H,1H-perfluorooctyl) perylene-3,4,9,10-tetracarboxylic acid diimide. Substituents attached to the imide nitrogens in the diimide structure comprise alkyl chains, electron deficient alkyl groups, and electron deficient benzyl groups, the chains preferably having a length of four to eighteen atoms. Devices based on materials having a perylene framework used as the organic semiconductor have led to low mobilities, for example $10^{-5}$ $cm^2/Vs$ for perylene tetracarboxylic dianhydride (PTCDA) and $1.5\times10^{-5}$ $cm^2/Vs$ for N,N'-diphenyl perylene tetracarboxylic acid diimide (PTCDI-Ph). See also U.S. Pat. Nos. 7,198,977 and 7,326,956 (Shukla et al.) for a description of perylene-based semiconductor materials in which the substituents on the imide nitrogens are aryl or phenylalkyl groups.

U.S. Patent Application Publication 2005/0176970 A1 (Marks et al.) discloses improved n-channel semiconductor films made of mono and diimide perylene and naphthalene compounds, nitrogen and core substituted with electron withdrawing groups. Substituents attached to the imide nitrogens in the diimide structure can be selected from alkyl, cycloalkyl, substituted cycloalkyl, aryl and substituted aryl moieties. However, Marks et al. do not see any comparative advantage of using cycloalkyl groups on the imide nitrogens. Accordingly, mobilities obtained from perylene diimides containing of N-octyl and N-cyclohexyl are virtually indistinguishable (page 10, Column 1, Example 10). Furthermore, the highest mobilities reported in this publication were 0.2 cm$^2$/Vs. Marks et al. show no experimental data with respect to naphthalene compounds, but require that their core be dicyano disubstituted.

Naphthalene tetracarboxylic diimides have been demonstrated to provide, as an n-type semiconductor, n-channel mobilities up to 0.16 cm$^2$/Vs using top-contact configured devices where the source and drain electrodes are on top of the semiconductor. Comparable results could be obtained with bottom contact devices, that is, where the source and drain electrodes are underneath the semiconductor, but a thiol underlayer needed to be applied between the electrodes, which had to be gold, and the semiconductor (see Katz et al. in *J. Am. Chem. Soc.* 2000 122, 7787, and in *Nature* 2000 404, 478). In the absence of the thiol underlayer, the mobility of the compounds of Katz et al. was found to be orders of magnitude lower in bottom-contact devices. EP1,041,653A1 (Katz et al.) and U.S. Pat. No. 6,387,727 (Katz et al.) disclose the use of fluorinated linear alkyl chain containing naphthalene 1,4,5,8-tetracarboxylic acid compounds in n-type TFT's. The highest mobilities obtained from a fluorinated linear alkyl chain containing naphthalene tetracarboxylic diimides in the noted U.S. patent was 0.06 cm$^2$/Vs, for N,N'-(1H, 1H-perfluorooctyl)-naphthalene-1,4,5,8-tetracarboxylic acid diimide. To achieve higher mobility, however, the TFT devices had to be fabricated at a higher substrate temperature (about 70° C.). When the devices were fabricated at room temperature, the mobility was only 0.01 cm$^2$/Vs.

Copending and commonly assigned U.S. Ser. No. 11/263, 111 (filed Oct. 31, 2005 by Shukla et al.) discloses a thin film of organic semiconductor material that comprises an N,N'-diaryl-substituted naphthalene-based tetracarboxylic diimide compound having a substituted or unsubstituted carbocyclic aromatic ring system directly attached to each imide nitrogen atom, wherein the substituents on at least one or both of the aromatic ring systems comprises at least one electron donating organic group.

U.S. Patent Application Publication 2006-0237712 A1 to Shukla et al. discloses a thin film of organic semiconductor material that comprises an N,N'-di(arylalkyl)-substituted naphthalene-based tetracarboxylic diimide compound having a substituted or unsubstituted carbocyclic aromatic ring system attached to each imide nitrogen atom through a divalent hydrocarbon group, wherein any optional substituents on the aryl rings comprises at least one electron donating organic group.

Copending and commonly assigned U.S. Ser. No. 11/285, 238 (filed Nov. 11, 2005 by Shukla et al.) discloses a thin film of organic semiconductor material that comprises an N,N'-dicycloalkyl-substituted naphthalene-1,4,5,8-bis(dicarboximide) compound having a substituted or unsubstituted aliphatic carbocyclic (alicyclic) ring system attached to each imide nitrogen atom in which an optional substituent or substituents on each ring comprises at least one electron donating organic group.

The above-mentioned organic thin films are capable of exhibiting, in the film form, the highest known field-effect electron mobility compared to reported values, up to 5.0 cm$^2$/Vs, for known n-type compounds.

Copending and commonly assigned U.S. Ser. No. 11/567, 954 (filed Dec. 7, 2006 by Shukla et al.) relates to the use of configurationally controlled N,N'-dicycloalkyl-substituted naphthalene-1,4,5,8-bis-carboximide compounds as semiconductor materials in n-channel semiconductor films for thin film transistors. The invention relates to the use of these materials in thin film transistors for electronic devices and methods of making such transistors and devices.

It is well understood in the art (e.g., *Stereochemistry of Organic Compounds*, E. L. Eliel, Chapter 8 (1962) McGraw-Hill Co.) that minimally constrained cyclohexane structures adopt a chair-like conformation as displayed herein below. In this chair conformation, ring hydrogens or substituents are disposed in either axial or equatorial orientations. The ring on the left in the FIGURE shows the A groups in the axial orientations, nearly perpendicular to the general plane of the cyclohexyl ring, while the B-groups are displayed in equatorial orientations, more nearly co-planar with the general plane of the ring. In the case depicted, the rings can interconvert via a well-understood process, with the two forms establishing an equilibrium mixture represented as follows:

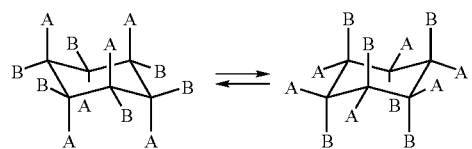

This mixture of the two chair forms can favor one conformation over the other based on the chemical nature of the substituents. Hypothetically, when A and B are the same, the mixture will be composed of 50% of each conformational component. When A and B are sufficiently different, however, the mixture may be viewed as completely one conformer. For example, in the case where a cyclohexane ring bears only one substituent, in virtually all known instances that substituent favors an equatorial orientation. In the general case of cyclohexane rings displaying two or more substituents, various conformational mixtures may result, depending on the chemical nature of those substituents. In the more specific case of 1,4-disubstituted cyclohexanes, the substituents may be stereochemically disposed either on the same side of the ring, the cis configuration, or on opposite sides of the cyclohexane ring, the trans configuration. In this latter case (the trans configuration) due to the above considerations, the two trans-substituents can adopt either an axial-axial or an equatorial-equatorial conformation, with this latter conformation predominating in virtually all known instances of such a case. In the former case (the cis configuration), due to the above considerations, the two cis-substituents can only adopt an axial-equatorial configuration, however, in which one of differing substituents can be either in the axial or equatorial position. More particularly, a substituent that is on the C-4 position relative to a larger ring system such as in a naphthalene tetracarboxylic diimide ring system, the conformation in which the larger ring system is equatorial and the C-4 substituent is axial tends to predominate The configuration as well as the conformations of substituted cyclohexane derivatives can be analyzed using a variety of spectroscopic techniques, e.g., see L. M. Jackman's *Applications of Nuclear Magnetic Resonance Spectroscopy in Organic Chemistry*, 2$^{nd}$ Edition, Pergamon Press (1969) p. 238. In practice the preparation of very pure cis or trans-1,4-substituted cyclohexanes can be problematic, and often mixtures, to some extent, of cis and trans substituted compounds are prepared. In the present case, mixtures that are more than 70 mole percent, preferably more than 80 mole percent, and more preferably more than 90 mole-percent trans will be considered essentially pure trans. Similarly, for the cis configuration, the term "essentially pure" will refer to the same mole percents, as determined by Nuclear Magnetic Resonance Spectroscopy (NMR).

PROBLEM TO BE SOLVED

As discussed above, a variety of 1,4,5,8-naphthalenetetracarboxylic acid diimides have been made and tested for n-type semiconducting properties. However, in general, TFT devices comprising these materials are very sensitive to oxygen and to obtain high mobilities, they must be operated in vacuum or under an atmosphere of argon. Furthermore, organic thin film transistor devices made using these materials usually exhibit high operational voltage (high threshold voltage). There is a need in the art for new 1,4,5,8-naphthalenetetracarboxylic acid diimide n-type semiconductor materials that are capable of exhibiting significant mobilities, lower threshold voltage and good current on/off ratios in organic thin film transistor devices when operated in air.

SUMMARY OF THE INVENTION

The present invention provides an article comprising, in a thin film transistor, a thin film of organic semiconductor material that comprises an N,N'-1,4,5,8-naphthalenetetracarboxylic acid diimide having at least one cycloalkyl group that has at least one fluorinated substituent containing one or more fluorine atoms at its 4-position.

In some embodiments, the thin film transistor in the article of this invention is a field effect transistor comprising a dielectric layer, a gate electrode, a source electrode and a drain electrode, and wherein the dielectric layer, the gate electrode, the thin film of organic semiconductor material, the source electrode, and the drain electrode are in any sequence as long as the gate electrode and the thin film of organic semiconductor material both contact the dielectric layer, and the source electrode and the drain electrode both contact the thin film of organic semiconductor material.

This invention also provides an electronic device that is an integrated circuit, active-matrix display, or solar cell that comprises a multiplicity of the thin film transistors of this invention.

Further, a process for fabricating a thin film semiconductor device, comprises, not necessarily in the following order, the steps of:

(a) depositing, onto a substrate, a thin film of n-channel organic semiconductor material that comprises an N,N'-1,4,5,8-naphthalenetetracarboxylic acid diimide having at least one cycloalkyl group that has a fluorinated substituent containing at least one fluorine at its 4-position, such that the organic semiconductor material exhibits a field effect electron mobility that is greater than 0.01 cm$^2$/Vs, (b) forming a spaced apart source electrode and drain electrode, wherein the source electrode and the drain electrode are separated by, and electrically connected with, the n-channel semiconductor film, and.

(c) forming a gate electrode spaced apart from the organic semiconductor material.

It has now been found that thin film transistors containing, as an n-type semiconductor, N,N'-1,4,5,8-naphthalenetetracarboxylic acid diimides bearing at least one cycloalkyl substituent which itself bears at least one fluorinated-substituent exhibit improved operational effectiveness and stability over other previously disclosed N,N'-1,4,5,8-naphthalenetetracarboxylic acid diimides bearing fluorinated imide substituents. The fluorinated substituent is a 4-substituent on those cyclohexyl rings and adopts predominantly an equatorial orientation in the trans configuration of the cyclohexyl ring and an axial orientation in the cis configuration of the cyclohexyl ring. Compared to fluorinated linear alkyl chain containing naphthalene 1,4,5,8-tetracarboxylic acid compounds, the thin film transistor devices comprising inventive materials exhibit improved electrical performance both under inert conditions and in air.

Accordingly, the present invention relates to n-channel semiconductor films for use in organic thin film transistors, comprising N,N'-naphthalene-1,4,5,8-bis(dicarboximide) compounds bearing at least one cycloalkyl substituent which itself bears at least one fluorinated-substituent, directly attached to (or substituted on) one of the two imide nitrogen atoms, an aliphatic carbocyclic ring system (that is, an alicyclic group having 4 to 10 carbons in the ring, for example, a cyclohexyl ring which has 6 carbon atoms in the ring), with the proviso that one of these alicyclic rings, referred to as the primary alicyclic ring, is necessarily a 4-substituted cyclohexyl ring relative to the attachment to the imide nitrogen (wherein the 4-substituent is the sole substituent relative to the imide attachment) in which such 4-substituent adopts either an essentially trans or essentially cis position, or both, to the imide nitrogen substituent. The other of the two alicyclic rings, other than the primary cycloalkyl ring, is referred to as the secondary alicyclic ring and may be independently substituted or unsubstituted. Substitution on one or optionally both aliphatic carbocyclic ring systems can include fluorinated-substituent that do not adversely effect the desired semiconductor properties of the material, it being understood that by "adversely effect" is meant results in a significantly or unduly adverse effect, since some tradeoff in desirable properties or marginal changes in properties may be acceptable as long as the desired effects are achieved. Semiconductor films made from such compounds are capable of exhibiting, in the film form, effective field-effect electron mobility, up to 1 cm$^2$/Vs or more when operated in air. Such semiconductor films are also capable of providing device on/off ratios in the range of 10$^5$ or more.

One aspect of the present invention is related to the use of such n-channel semiconductor films in organic thin film transistors each comprising spaced apart first and second contact means connected to an n-channel semiconductor film. A third contact means can be spaced from said first and second contact means and adapted for controlling, by means of a voltage applied to the third contact means, a current between the first and second contact means through said film. The first, second, and third contact means can correspond to a drain, source, and gate electrode in a field effect transistor.

Another aspect of the present invention is directed to a process for fabricating a thin film transistor, preferably by sublimation or solution-phase deposition of the n-channel semiconductor film onto a substrate, wherein the substrate temperature is preferably at a temperature of no more than 100° C. during the deposition.

In one embodiment of the present invention, a thin film transistor in which a thin film of organic semiconductor material comprises a N,N'-1,4,5,8-naphthalenetetracarboxylic acid diimides bearing cycloalkyl substituents at least one of such cycloalkyl substituent itself bears at least one fluorinated-substituent with the proviso that one of these alicyclic rings is necessarily a 4-substituted cyclohexyl ring which is the sole substituent other than the imide attachment; with such substituent adopting (only one of) either an essentially trans or an essentially cis position, respectively, to the imide nitrogen substituent.

Advantageously, an n-channel semiconductor film used in a transistor device according to the present invention does not necessarily require as in certain prior art devices, in order to obtain high mobilities, prior treatment of the first and second contact means connected to the film, which treatment is optional. Furthermore, the compounds used in the present invention possess significant volatility so that vapor phase deposition, where desired, is available to apply the n-channel semiconductor films to a substrate in an organic thin film transistor.

DESCRIPTION OF THE INVENTION

As used herein, "a" or "an" or "the" are used interchangeably with "at least one," to mean "one or more" of the element being modified.

As used herein, the terms "over," "above," and "under" and the like, with respect to layers in the organic thin film transistor, refer to the order of the layers, wherein the organic thin film layer is above the gate electrode, but do not necessarily indicate that the layers are immediately adjacent or that there are no intermediate layers.

Figure 1:
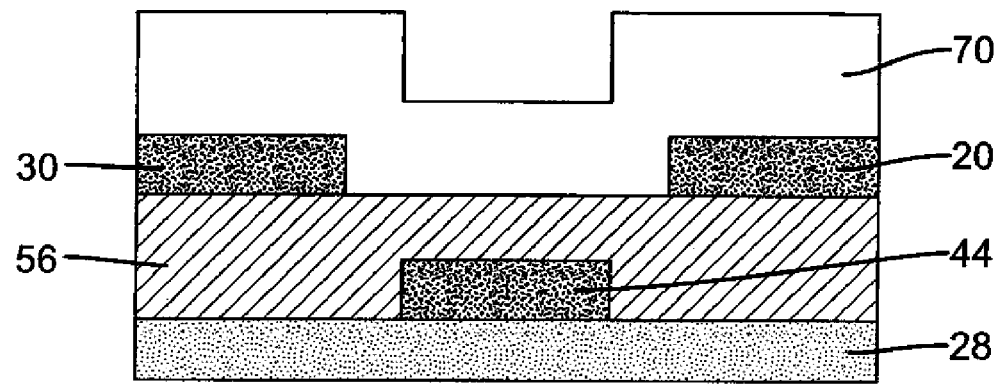
FIG. 1 illustrates a cross-sectional view of a typical organic thin film transistor having a bottom contact configuration.
Figure 2:
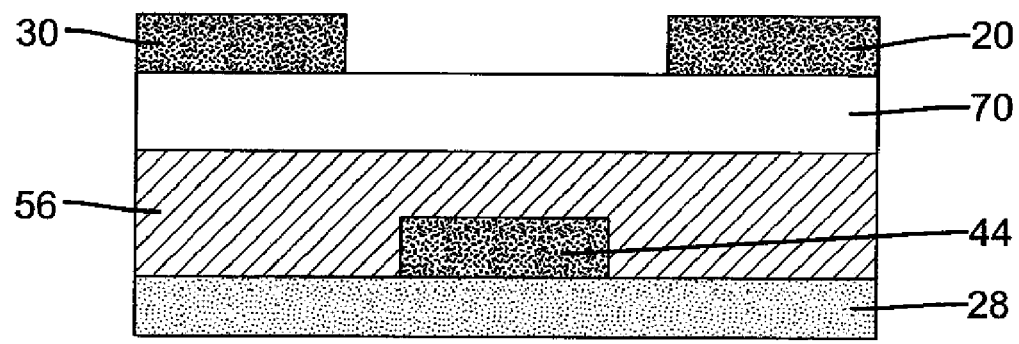
FIG. 2 illustrates a cross-sectional view of a typical organic thin film transistor having a top contact configuration.

Cross-sectional views of typical organic thin film transistor are shown in FIGS. 1 and 2 wherein FIG. 1 illustrates a typical bottom contact configuration and FIG. 2 illustrates a typical top contact configuration.

Each thin film transistor (TFT) in the embodiments of FIGS. 1 and 2 contains a source electrode 20, a drain electrode 30, a gate electrode 44, a gate dielectric 56, a substrate 28, and the semiconductor 70 of the invention in the form of a film connecting the source electrode 20 to drain electrode 30, which semiconductor comprises a compound selected from the class of configurationally controlled N,N'-dicycloalkyl-substituted naphthalene-1,4,5,8-bis(dicarboximide) compounds described herein.

When the TFT operates in an accumulation mode, the charges injected from the source electrode into the semiconductor are mobile and a current flows from source to drain, mainly in a thin channel region within about 100 Angstroms of the semiconductor-dielectric interface. See A. Dodabalapur, L. Torsi H. E. Katz, *Science* 1995, 268, 270, hereby incorporated by reference. In the configuration of FIG. 1, the charge need only be injected laterally from the source electrode 20 to form the channel. In the absence of a gate field the channel ideally has few charge carriers; as a result there is ideally no source-drain conduction.

The off current is defined as the current flowing between the source electrode 20 and the drain electrode 30 when charge has not been intentionally injected into the channel by the application of a gate voltage. For an accumulation-mode TFT, this occurs for a gate-source voltage more negative, assuming an n-channel, than a certain voltage known as the threshold voltage [see Sze in *Semiconductor Devices—Physics and Technology*, John Wiley & Sons (1981), pages 438-443]. The on current is defined as the current flowing between the source electrode 20 and the drain electrode 30 when charge carriers have been accumulated intentionally in the channel by application of an appropriate voltage to the gate electrode 44, and the channel is conducting. For an n-channel accumulation-mode TFT, this occurs at gate-source voltage more positive than the threshold voltage. It is desirable for this threshold voltage to be zero, or slightly positive, for n-channel operation. Switching between on and off is accomplished by the application and removal of an electric field from the gate electrode 44 across the gate dielectric 56 to the semiconductor-dielectric interface, effectively charging a capacitor.

In accordance with the invention, the organic semiconductor materials used in the present invention, when used in the form of an n-channel film, can exhibit high performance in inert as well as ambient conditions without the need for optional special chemical underlayers.

The improved n-channel semiconductor film of the present invention, comprising a N,N'-1,4,5,8-naphthalenetetracarboxylic acid diimides bearing cycloalkyl substituents at least one of such cycloalkyl substituent itself bears at least one fluorinated-substituent described herein, are capable of exhibiting a field effect electron mobility greater than 0.001 $cm^2/Vs$, preferably greater than 0.01 $cm^2/Vs$. More preferably films comprising the compounds of the present invention exhibit a field effect electron mobility that is greater than 0.1 $cm^2/Vs$.

In another embodiment of the present invention, n-channel semiconductor film of the present invention comprising a N,N'-1,4,5,8-naphthalenetetracarboxylic acid diimides bearing cycloalkyl substituents at least one of such cycloalkyl substituent itself bears at least one fluorinated-substituent described herein, are capable of exhibiting lower operational voltage ($V_{th}$)

In addition, the n-channel semiconductor film of the invention is capable of providing on/off ratios of at least $10^4$, advantageously at least $10^5$. The on/off ratio is measured as the maximum/minimum of the drain current as the gate voltage is swept from zero to 100 volts and the drain-source voltage is held at a constant value of 100 volts, and employing a silicon dioxide gate dielectric.

Moreover, these properties are attainable after repeated exposure of the n-type semiconductor material to air, before film deposition exposure of the transistor device and/or the channel layer to air after deposition, as well as during the device operation.

Without wishing to be bound by theory, there are several factors that are believed to contribute to the desirable properties of the naphthalene-based tetracarboxylic acid diimide compounds of the present invention. The solid-state structure of the material has the individual molecules packed such that the orbitals of the conjugated naphthalene core system containing the naphthalene ring system and/or the imide carboxyl groups are able to interact with adjacent molecules, resulting in high mobility. The direction of this interaction has a component parallel to the direction of desired current flow in a device using this material as the active layer. The morphology of the films formed by the material is substantially continuous, such that current flows through the material without unacceptable interruption. The substituent stereochemistry as controlled in the molecules of the invention does not disrupt the intrinsic ability of these molecules to pack in an effective crystalline motif.

The lowest lying unoccupied molecular orbital of the compound is at an energy that allows for injection of electrons at useful voltages from metals with reasonable work functions. This conjugated structure generally has a desirable lowest unoccupied molecular orbital (LUMO) energy level of about 3.5 eV to about 4.6 eV with reference to the vacuum energy level. As known in the art, LUMO energy level and reduction potential approximately describe the same characteristics of a material. LUMO energy level values are measured with reference to the vacuum energy level, and reduction potential values are measured in solution versus a standard electrode. An advantage for device applications is that the LUMO in the crystalline solid, which is the conduction band of the semiconductor, and the electron affinity of the solid both are measured with reference to the vacuum level. The latter parameters are usually different from the former parameters, which are obtained from solution.

As indicated above, the present invention is directed to an article comprising a thin film transistor in which a thin film of organic semiconductor material comprises N,N'-1,4,5,8-naphthalenetetracarboxylic acid diimides bearing cycloalkyl substituents at least one of such cycloalkyl substituent itself bears at least one fluorinated-substituent directly to each imide nitrogen atom. The two alicyclic ring systems can differ, and the secondary alicyclic ring system can independently have different substitution, additional substitution, or no substitution. For example, each alicyclic ring system is the same, although the substitution on each ring system may differ.

In one embodiment of the present invention, a class of N,N'-dicycloalkyl-substituted naphthalene-based tetracarboxylic diimide compounds represented by the following general Structure I:

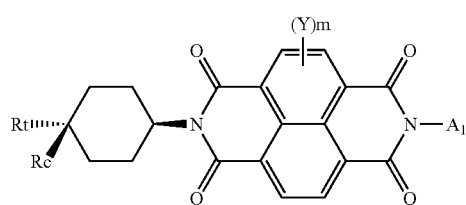

I

In the above structures, it will be evident that a boldly (triangularly) solid bond lines attached to the cyclohexyl ring represent a bond coming towards the viewer while a dotted bond line represents a bond going away from the viewer, such that the boldly solid line in Structure I represents a cis configuration and one dotted bond line in Structure I represents a trans configuration.

In Structure I, $R_c$ represents a fluorinated substituent in the C-4 cis configuration with respect to the imide group, and $R_t$ represents a fluorinated substituent in the C-4 trans configuration with respect to the imide group, $A_1$ is any organic substituent such as a monocyclic ring or bicyclic alicyclic hydrocarbon ring, Y groups are independently selected organic or inorganic groups that do not adversely affect the n-type semiconductor properties of the film made from such compounds, and m is any integer from 0 to 4.

$R_c$ and $R_t$ can be the same or different fluorinated substituents including but not limited to, fluorinated linear or branched alkyl groups having 1 to 20 carbons (typically from 1 to 10 carbon atoms). Particularly useful are fluorinated alkyl groups having 1 to 6 carbon atoms.

More particularly, $A_1$ is a substituted or unsubstituted alicyclic ring system comprising 4 to 10 carbons in the ring. For example, the alicyclic ring systems are unbridged monocyclic or bridged bicyclic ring systems. Examples of alicyclic ring systems include cyclobutyl, cyclopentyl, cyclohexyl, or cycloheptyl, as well as bridged alicyclic hydrocarbon systems such as bicyclo [4.4.0] decane. $A_1$ can be a substituted or unsubstituted cyclohexyl ring, which if having two or more substituents can be cis, trans, or a cis-trans mixture (if A1 does not have a second substituent, then cis and trans isomerism nomenclature does not readily apply), it being understood that the normal bond line to the $A_1$ ring system includes the possibility of essentially trans configuration, essentially cis configuration, an otherwise mixture of the two between molecules, a mixture within the same molecule (if more than two substituents), or the absence of cis-trans configuration on the $A_1$ ring altogether (if not more than one substituent, not including hydrogen). Two substituents on A1 can form a fused aryl or cycloalkyl ring that in turn can be substituted or unsubstituted. For example, $A_1$ can be a ring system that is a substituted or unsubstituted cyclohexyl or cyclopentyl ring.

Alternatively, $A_1$ can be the same or different fluorinated substituent as $R_c$, such as a saturated fluoroalkyl group having 1 to 5 carbon atoms.

In Structure I, the Y groups are independently selected from any suitable groups. The Y substituent groups on the naphthalene nucleus can include, for example, alkyl groups, alkenyl, alkoxy groups, aryl groups, arylalkyl groups, halogens such as fluorine or chlorine, cyano, fluorine-containing groups such as $CF_3$, carbonyl-containing or carboxy-containing groups, or any other groups that do not affect the n-type semiconductor properties of the film made from such compounds. Y groups can also be selected from any of the R groups mentioned below. It is advantageous to avoid substituents that tend to interfere with close approach of the conjugated cores of the compounds in a stacked arrangement of the molecules that is conducive to semiconductor properties. Such substituents to be avoided include highly branched groups, ring structures and groups having more than 12 atoms, particularly where such groups or rings would be oriented to pose a significant steric barrier to the close approach of the conjugated cores. In addition, substituent groups are less preferred or should be avoided that substantially lower the solubility and/or volatility of the compounds such that the desirable fabrication processes are prevented. For example, the Y groups can be selected from the group consisting of alkyl, alkenyl, alkoxy, aryl, arylalkyl, fluorine, chlorine, cyano, fluorine-containing alkyl, carbonyl-containing, and carboxy-containing groups.

In the above Structure I, a primary and a secondary dicarboxylic imide moiety is attached on opposite sides of the naphthalene nucleus, at the 1,4- and 5,8-positions of the naphthalene nucleus. The naphthalene nucleus can be optionally substituted with up to four independently selected Y groups, wherein m is any integer from 0 to 4. For example, Y groups are independently selected from suitable groups that do not unduly adversely affect the n-type semiconductor properties of the film made from such compounds.

In some embodiments, the thin film or organic semiconductor material comprises an N,N'-fluorinated dicycloalkyl substituted 1,4,5,8-naphthalene-tetracarboxylic diimide compounds represented by Structures II(a) and (b):

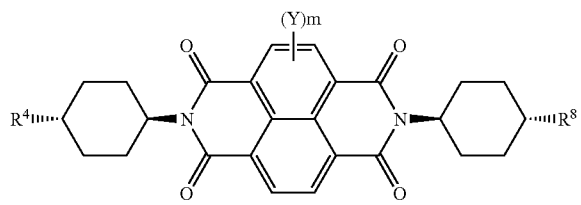

II (a)

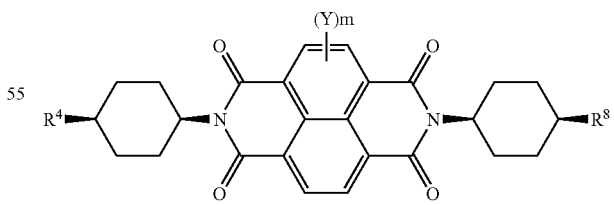

II (b)

wherein $R^4$ (on the primary cyclohexyl ring) is any suitable organic substituent as defined above, and $R^8$ (on the secondary cyclohexyl ring system) is independently H or any fluorine containing substituent. Each of $R^4$ and $R^8$, if substituted, are either one, but only one, of an essentially trans or cis configuration with respect to the attachment to the imine nitrogen. In this particular embodiment, the cyclohexyl ring in Structures II(a) and (b) other than the 4-substituted cyclohexyl ring is either not substituted or, like the 4-substituted cyclohexyl ring, has a sole fluorine containing substituent other than the attachment at the imine nitrogen, that is, both of the primary and secondary cyclohexyl ring systems in the compound comprise a single substituent other than the attachment at the imine nitrogen. Thus, both alicyclic rings are configurationally controlled in Structures II(a) and II(b). The Y groups are described above.

Examples of particular compounds useful in the present invention include N,N'-bis(trans-4-trifluoromethyl-cyclohexyl)-naphthalene-1,4,5,8 tetracarboxylic acid diimide, N-(trans-4-methyl-cyclohexyl), N'-(trans-4-trifluoromethyl-cyclohexyl)-naphthalene-1,4,5,8 tetracarboxylic acid diimide, N-cyclohexyl-N'-(trans-4-trifluoromethyl-cyclohexyl)-naphthalene-1,4,5,8 tetracarboxylic acid diimide, N,N'-bis(trans-4-perfluorobutyl-cyclohexyl)-naphthalene-1,4,5,8 tetracarboxylic acid diimide or N,N'-bis(cis-4-trifluoromethyl-cyclohexyl)-naphthalene-1,4,5,8-tetracarboxylic acid diimide.

In Structures II(a) and II(b) above, substituent $R^4$ or $R^8$ or any optional additional substituents on the secondary alicyclic ring can, for example, be selected from fluorine containing organic or inorganic groups. Suitable groups include but are not limited to fluoroalkyl groups, fluorocycloalkyl, fluoroalkenyl, fluoroalkoxy groups, fluorinated aryl groups, fluoralkyl substituted aryl groups, fluorine-containing groups such as $CF_3$, carbonyl-containing or carboxy-containing groups, or any other groups that do not significantly adversely affect the n-type semiconductor properties of the film made from such compounds. Preferred organic groups include, for example, a partially or completely fluorinated $C_1$-$C_8$ organic substituent, more preferably a partially or completely fluorinated $C_1$-$C_4$ organic substituent, most preferably fluorinated alkyl substituents. More specific examples of organic groups include, for example, $CF_3$, linear or branched $C_2$-$C_8$ fluoroalkyl, $C_1$-$C_8$ fluorinated alkylene (a monovalent unsaturated aliphatic hydrocarbon), fluoro-substituted phenyl or hexyl, or $C_1$-$C_8$ alkoxy, $C_1$-$C_8$ carbonyl and carboxy substituents. Preferred inorganic groups include fluorine, and fluoroalkyl for example. Also envisioned are $R^8$ groups that are themselves an N,N'-cycloalkyl-substituted naphthalene-1,4,5,8-bis-carboximide moiety in which one of the imide nitrogen groups in the $R^8$ group is the point of attachment to the cyclohexyl group either directly or indirectly, for example bis compounds based on a central moiety (for example, comprising the secondary cyclohexyl ring, as in Compound I-13 or I-16 below) that is disubstituted with two N,N'-cycloalkyl-substituted naphthalene-1,4,5,8-bis-carboximide moieties.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituents unsubstituted form, but also its form to the extent it can be further substituted (up to the maximum possible number) with any other mentioned substituent group or groups (mentioned for the same position) so long as the substituent does not destroy properties necessary for semiconductor utility. If desired, the substituents may themselves be further substituted one or more times with acceptable substituent groups. For example, an alkyl group can be substituted with an alkoxy group or one or more fluorine atoms, in the case of $R^4$ or $R^8$ or other R group (optional additional substituents in the secondary alicyclic ring, four additional R groups in the case where the secondary alicyclic ring is a cyclohexyl ring) or in the case of a Y group. When a molecule may have two or more substituents, the substituents may be joined together to form an aliphatic or unsaturated ring unless otherwise provided.

With respect to the R groups or Y groups, examples of any of the above-mentioned alkyl groups, except as otherwise indicated, are methyl, ethyl, propyl, isopropyl, butyl, isobutyl, t-butyl, pentyl, hexyl, octyl, 2-ethylhexyl, and congeners. Alkyl groups having 1 to 6 carbon atoms, typically 1 to 4 carbon atoms, are intended to include branched or linear groups. Alkenyl groups can be vinyl, 1-propenyl, 1-butenyl, 2-butenyl, and congeners.

With respect to Y groups, aryl groups can be phenyl, naphthyl, styryl, and congeners. Aralkyl groups can be benzyl, phenethyl, and congeners. Useful substituents on any of the foregoing include alkoxy and the like.

Specific illustrative examples of useful N,N'-bicycloalkyl-substituted naphthalene-1,4,5,8-bis(dicarboximide) derivatives are shown, but not limited, by the compounds I-1 through I-9 shown below:

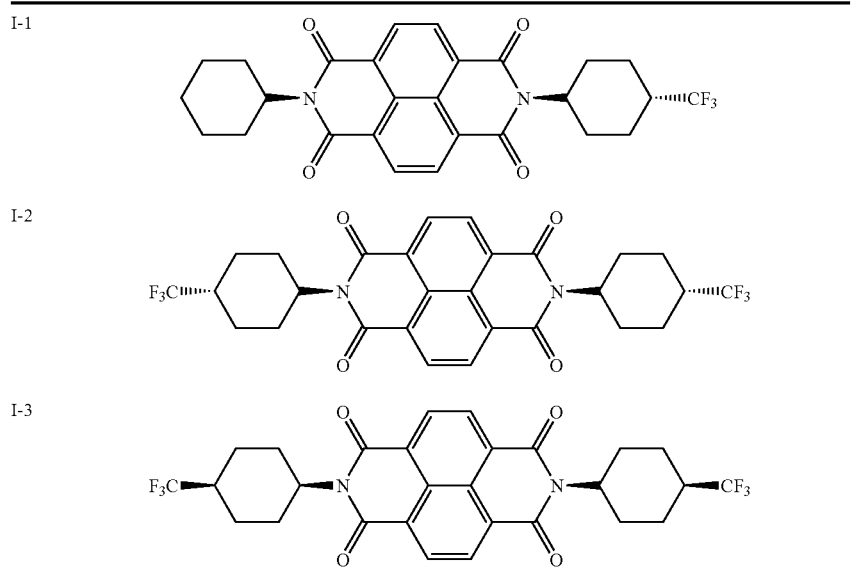

-continued

I-4
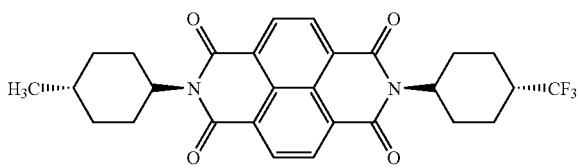

I-5
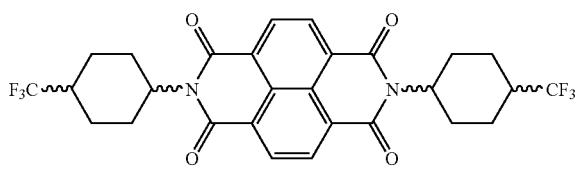

I-6
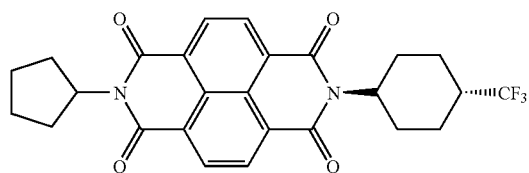

I-7
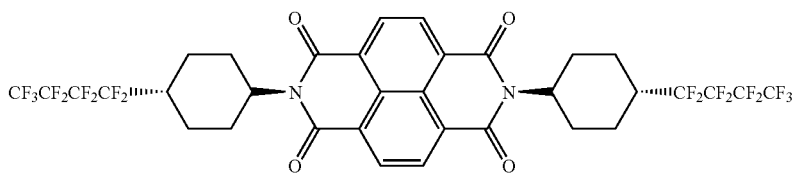

I-8
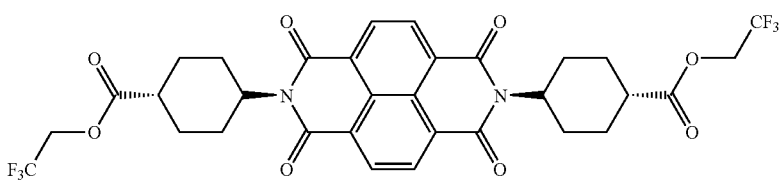

I-9
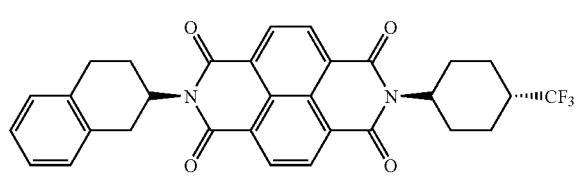

N,N'-fluorosubstituted dicycloalkyl-substituted naphthalene-1,4,5,8-bis(dicarboximide) compounds used in this invention can be conveniently prepared, for example, by reacting, at an elevated temperature for a sufficient period of time, a mixture of commercially available 1,4,5,8-naphthalenetetracarboxylic acid anhydride and a (cis or trans) 4-trifluoroalkyl substituted cyclohexylamine in a suitable solvent. The skilled artisan can thereby obtain using conventional techniques involving separation and purification, the desired product. The resulting material can be proved to be homogenous and characterized by the desired structural configuration by standard chromatographic and spectral determinations.

Similarly, a compound having different alicyclic rings can be prepared by reacting a mixture of known 1,8-N-cyclohexylcarboximido-4,5-naphthalenedicarboxylic acid anhydride with a configurationally controlled 4-fluorinated alkyl substituted cyclohexylamine in solvent. The resulting slurry can be filtered; washed, air dried, and recrystallized as appropriate to provide the desired product as a solid material that is consistent with its assigned structure.

The specific preparations described below in the Examples are included for reference, by analogy, also as general methods for the preparation of various compounds of the invention. These methods are not meant to be limiting, however, since compounds of the invention can prepared by other methods or my minor variants of the included procedures, including via well-established methods in the art.

Another aspect of the invention relates to the process for the production of semiconductor components and electronic devices incorporating such components. In one embodiment, a substrate is provided and a layer of the semiconductor material as described above can be applied to the substrate, electrical contacts being made with the layer. The exact process sequence is determined by the structure of the desired semiconductor component. Thus, in the production of an organic field effect transistor, for example, a gate electrode can be first deposited on a flexible substrate, for example an organic polymer film, the gate electrode can then be insulated with a dielectric and then source and drain electrodes and a layer of the n-channel semiconductor material can be applied on top. The structure of such a transistor and hence the sequence of its production can be varied in the customary manner known to a person skilled in the art. Thus, alternatively, a gate electrode can be deposited first, followed by a gate dielectric, then the organic semiconductor can be applied, and finally the contacts for the source electrode and drain electrode deposited on the semiconductor layer. A third structure could have the source and drain electrodes deposited first, then the organic semiconductor, with dielectric and gate electrode deposited on top.

The skilled artisan will recognize other structures can be constructed and/or intermediate surface modifying layers can be interposed between the above-described components of the thin film transistor. In most embodiments, a field effect transistor comprises an insulating layer, a gate electrode, a semiconductor layer comprising an organic material as described herein, a source electrode, and a drain electrode, wherein the insulating layer, the gate electrode, the semiconductor layer, the source electrode, and the drain electrode are in any sequence as long as the gate electrode and the semiconductor layer both contact the insulating layer, and the source electrode and the drain electrode both contact the semiconductor layer.

A support can be used for supporting the OTFT during manufacturing, testing, and/or use. The skilled artisan will appreciate that a support selected for commercial embodiments may be different from one selected for testing or screening various embodiments. In some embodiments, the support does not provide any necessary electrical function for the TFT. This type of support is termed a "non-participating support" in this document. Useful materials can include organic or inorganic materials. For example, the support may comprise inorganic glasses, ceramic foils, polymeric materials, filled polymeric materials, coated metallic foils, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS), and fiber-reinforced plastics (FRP).

A flexible support is used in some embodiments of the present invention. This allows for roll processing which may be continuous, providing economy of scale and economy of manufacturing over flat and/or rigid supports. The flexible support chosen preferably is capable of wrapping around the circumference of a cylinder of less than about 50 cm diameter, more preferably 25 cm diameter, most preferably 10 cm diameter, without distorting or breaking, using low force as by unaided hands. The preferred flexible support may be rolled upon itself.

In some embodiments of the invention, the support is optional. For example, in a top construction as in FIG. 2, when the gate electrode and/or gate dielectric provides sufficient support for the intended use of the resultant TFT, the support is not required. In addition, the support may be combined with a temporary support. In such an embodiment, a support may be detachably adhered or mechanically affixed to the support, such as when the support is desired for a temporary purpose, e.g., manufacturing, transport, testing, and/or storage. For example, a flexible polymeric support may be adhered to a rigid glass support which support could be removed.

The gate electrode can be any useful conductive material. A variety of gate materials known in the art, are also suitable, including metals, degenerately doped semiconductors, conducting polymers, and printable materials such as carbon ink or silver-epoxy. For example, the gate electrode may comprise doped silicon, or a metal, such as aluminum, chromium, gold, silver, nickel, palladium, platinum, tantalum, and titanium. Conductive polymers also can be used, for example polyaniline, poly(3,4-ethylenedioxythiophene)/poly(styrene sulfonate) (PEDOT:PSS). In addition, alloys, combinations, and multilayers of these materials may be useful.

In some embodiments of the invention, the same material can provide the gate electrode function and also provide the support function of the support. For example, doped silicon can function as the gate electrode and support the OTFT.

The gate dielectric is provided on the gate electrode. This gate dielectric electrically insulates the gate electrode from the balance of the OTFT device. Thus, the gate dielectric comprises an electrically insulating material. The gate dielectric should have a suitable dielectric constant that can vary widely depending on the particular device and circumstance of use. For example, a dielectric constant from about 2 to 100 or even higher is known for a gate dielectric. Useful materials for the gate dielectric may comprise, for example, an inorganic electrically insulating material. The gate dielectric may comprise a polymeric material, such as polyvinylidene difluoride (PVDF), cyanocelluloses, polyimides, etc. The gate electric may comprise a plurality of layers of different materials having different dielectric constants.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these examples can be used for the gate dielectric. Of these materials, aluminum oxides, silicon oxides, and zinc selenide are preferred. In addition, polymeric materials such as polyimides, and insulators that exhibit a high dielectric constant. Such insulators are discussed in U.S. Pat. No. 5,981,970 (Dimitrakopoulos et al.) hereby incorporated by reference.

The gate dielectric can be provided in the OTFT as a separate layer, or formed on the gate such as by oxidizing the gate material to form the gate dielectric. The dielectric layer may comprise two or more layers having different dielectric constants.

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof and multilayers thereof.

The thin film electrodes (for example, gate electrode, source electrode, and drain electrode) can be provided by any useful means such as physical vapor deposition (for example, thermal evaporation, sputtering) or ink jet printing. The patterning of these electrodes can be accomplished by known methods such as shadow masking, additive photolithography, subtractive photolithography, printing, microcontact printing, and pattern coating.

The organic semiconductor layer can be provided over or under the source and drain electrodes, as described above in reference to the thin film transistor article. The present invention also provides an integrated circuit comprising a plurality of OTFT's made by the process described herein. The n-channel semiconductor material made using the above-described N,N'-bis(fluoroalkylcycloalkyl) naphthalene-1,4,5,8-bis(dicarboximide) compounds are capable of being formed on any suitable substrate which can comprise the support and any intermediate layers such as a dielectric or insulator material, including those known in the art.

The entire process of making the thin film transistor or integrated circuit of the present invention can be carried out below a maximum support temperature of about 450° C., for example below about 250° C., or typically below about 150° C. or below about 100° C. The temperature selection generally depends on the support and processing parameters known in the art, once one is armed with the knowledge of the present invention contained herein. These temperatures are well below traditional integrated circuit and semiconductor processing temperatures, which enables the use of any of a variety of relatively inexpensive supports, such as flexible polymeric supports. Thus, the invention enables production of relatively inexpensive integrated circuits containing organic thin film transistors with significantly improved performance.

Compounds used in the invention can be readily processed and are thermally stable to such as extent that they can be vaporized. The compounds possess significant volatility, so that vapor phase deposition, where desired, is readily achieved. Such compounds can be deposited onto substrates by vacuum sublimation.

Deposition by a rapid sublimation method is also possible. One such method is to apply a vacuum of 35 mtorr to a chamber containing a substrate and a source vessel that holds the compound in powdered form, and heat the vessel over several minutes until the compound sublimes onto the substrate. Generally, the most useful compounds form well-ordered films, with amorphous films being less useful.

Devices in which the n-channel semiconductor films of the invention are useful include especially thin film transistors (TFT's), especially organic field effect thin-film transistors. Also, such films can be used in various types of devices having organic p-n junctions, such as described on pages 13 to 15 of U.S. Patent Application Publication 2004/0021204 A1 (Liu) that is hereby incorporated by reference.

Electronic devices in which TFT's and other devices are useful include, for example, more complex circuits, e.g., shift registers, integrated circuits, logic circuits, smart cards, memory devices, radio-frequency identification tags, backplanes for active matrix displays, active-matrix displays (e.g. liquid crystal or OLED), solar cells, ring oscillators, and complementary circuits, such as inverter circuits, for example, in combination with other transistors made using available p-type organic semiconductor materials such as pentacene. In an active matrix display, a transistor according to the present invention can be used as part of voltage hold circuitry of a pixel of the display. In devices containing the TFT's of the present invention, such TFT's are operatively connected by means known in the art.

The present invention further provides a method of making any of the electronic devices described above. Thus, the present invention is embodied in an article that comprises one or more of the TFT's described.

Advantages of the invention will be demonstrated by the following examples that are intended to be representative and not limiting of the present invention.

EXAMPLES

A. Material Synthesis

The symmetric N,N'-bis(cycloalkyl)-substituted naphthalene-1,4,5,8-bis(dicarboximide) compounds useful in this invention are conveniently prepared by the cyclization of naphthalene 1,4,5,8-tetracarboxylic acid dianhydride with excess fluoroalkyl-substituted cycloalkylamine (RfNH$_2$) following a general method as described in Rademacher, A. et al. *Chem. Ber.* 1982 115, 2927 or minor variants thereof. As examples of a typical synthetic procedure, the preparations of compounds I-2, I-3, I-4, and C-1 are described herein.

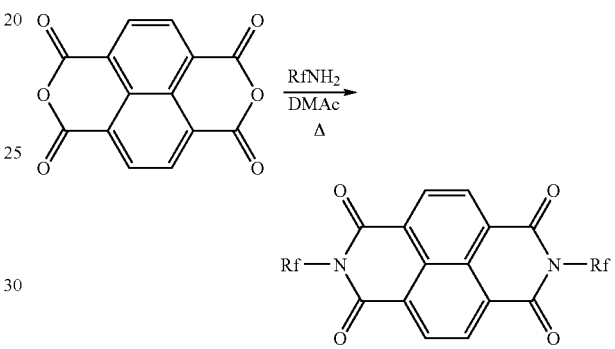

In turn, the essential fluoro-substituted cycloalkylamines can be prepared by variety methods well known in the art. Included as illustration are the preparations of trans-4-trifluoromethylcyclohexylamine and cis-4 trifluoromethylcyclohexylamine.

Non-symmetrically substituted naphthalene-1,4,5,8-bis(dicarboxide) compounds used in this invention can be prepared in a similar manner to the above substituting the requisite naphthalene-1,8-carboximide-4,5-dicarboxylic acid anhydride for the naphthalen-1,4,5,8-tetracarboxylic acid dianhydride (vide infra).

Other selected compounds of the invention were prepared in an analogous manner using similar procedures common to the art.

Preparation of Compound I-2:

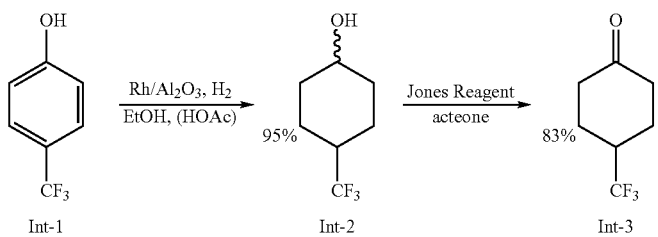

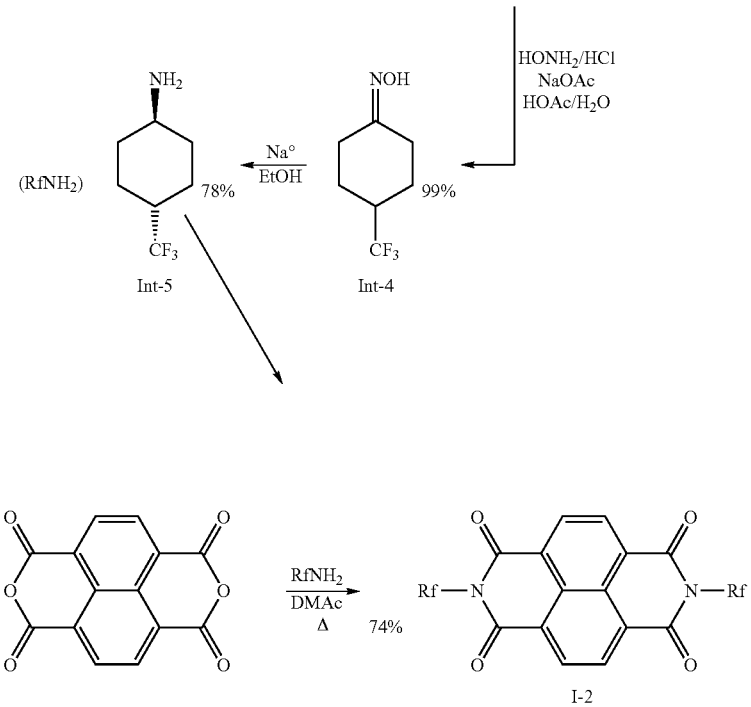

Preparation of Int-2:

A mixture of Int-1 (CAS 402-45-9; 25.0 g, 0.154 mole), 2 ml of acetic acid, and 2.0 g of 10% rhodium-on-alumina in 200 ml of ethanol were shaken at ambient temperature on a Parr® apparatus under hydrogen pressure ($P_0$=52 psi) for 16 hours. The mixture was filtered to remove the catalyst, and then the filtrate was concentrated in vacuo to provide Int-2 as a mixture of isomeric alcohols (24.7 g, 95%). This material displayed spectral characteristics consistent with its assigned structure.

Preparation of Int-3:

A solution of Int-2 (24.7 g, 0.147 mole) in 250 ml of acetone was chilled in an ice water bath and treated with Jones' reagent (chromic acid in sulfuric acid, 46 ml) such that the reaction temperature remained at or below 25° C. After the addition, the mixture stirred at reduced temperature for 15 minutes and at ambient temperature for 45 minutes. The mixture was treated with isopropyl alcohol (IPA) to destroy remaining oxidant and the teal colored mixture treated with diatomaceous earth and diluted with isopropyl ether (IPE). The whole mixture was filtered, the solids were washed with IPE, and the combined filtrates were concentrated in vacuo. The residue was partitioned between water and IPE. The organics were dried and concentrated in vacuo to provide Int-3 as a colorless oil (20.0 g, 83%). This material displayed spectral characteristics consistent with its assigned structure.

Preparation of Int-4:

A mixture of Int-3 (19.0 g, 0.114 mole), hydroxylamine hydrochloride (11.8 g, 0.169 mole), and sodium acetate (14.2 g, 0.173 mole) in 50 ml of ethanol and 70 ml of water, was heated at reflux for 3 hours. The mixture was cooled then extracted with ethyl acetate. The organics were dried and concentrated in vacuo. Portions of toluene (3 times 150 ml) were added and flashed off, to provide Int-4 as a colorless solid (20.5 g, 99%). This material displayed spectral characteristics consistent with its assigned structure.

Preparation of Int-5:

A solution of Int-4 (18.1 g, 0.100 mole) in 350 ml of ethanol was heated to reflux, and then was cautiously treated over 10 minutes with sodium metal pieces (35 g, 1.5 g-atom) to maintain a vigorous reflux. After the addition, the mixture was heated at reflux for an additional hour, and then cooled. The thick mixture was treated with a 140 ml of hydrochloric acid (T≦55° C.) and 140 ml of water. The thick mixture was concentrated in vacuo. The solid was washed with IPE to remove residual neutral impurities. The resulting solid was suspended in 250 ml of water and 250 ml of IPE and the solution pH adjusted via addition of 50% aqueous sodium hydroxide (pH≧13). The organic layer was separated, dried and concentrated in vacuo to afford Int-5 as a cloudy near colorless oil (12.9 g, 78%). This material displayed spectral characteristics consistent with its assigned structure.

Preparation of I-2:

A slurry of naphthalene-1,4,5,8-tetracarboxylic acid dianhydride (CAS 81-30-1; 0.67 g, 2.5 mmol) in 10 ml of N,N-dimethylacetamide (DMAc) was treated with Int-5 (1.0 g, 6 mmol). The homogenous mixture was sealed in a pressure vessel then heated at 135-140° C. for 1 hour and then cooled. The resulting slurry was diluted with several volumes of methanol and filtered. The isolated solid was washed with methanol and air-dried to provide I-2 as a peach solid. This solid was recrystallized from 50 ml of DMAc to give I-2 as a pink solid (1.05 g, 74%). This material displayed spectral characteristics consistent with its assigned structure.

Preparation of Compound I-3:

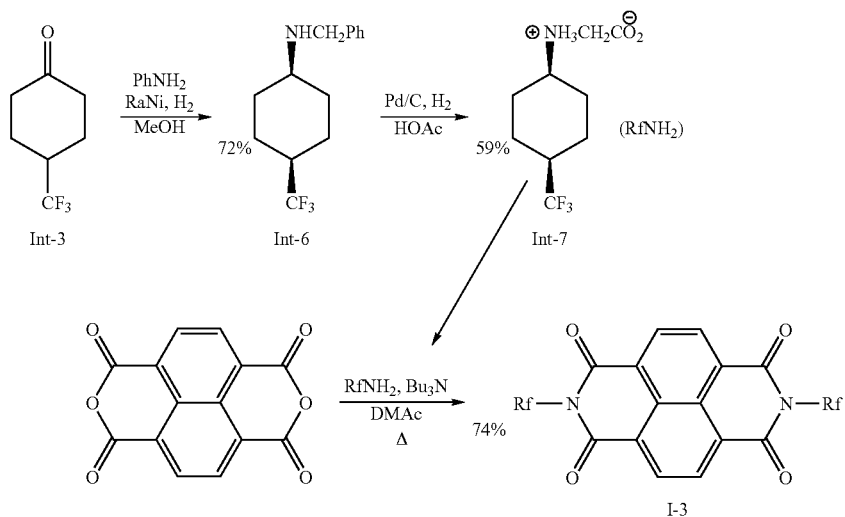

Preparation of Int-6:

A mixture of Int-3 (17.1 g, 0.103 mole), benzylamine (16.3 g, 0.152 mole), 5 g Raney® nickel catalyst, and 250 ml of methanol were shaken at ambient temperature on a Parr Apparatus® under hydrogen pressure ($P_0$=50 psi) for two days. The mixture was cautiously filtered, the solids washed with methanol. The combined filtrate was concentrated in vacuo. The residue was passed through silica gel, eluting with methylene chloride, to afford Int-6 as a colorless oil (19.0 g, 72%). This material displayed spectral characteristics consistent with its assigned structure.

Preparation of Int-7:

A mixture of Int-6 (18.0 g, 70.0 mmol) and 1.5 g 10% palladium-on-carbon in 150 ml of acetic acid was shaken at 60° C. on a Parr® apparatus under hydrogen pressure ($P_0$=50 psi) for one day. The mixture was filtered, the solids washed with acetic acid. The combined filtrate was concentrated in vacuo. Xylenes were flashed off to remove traces of acetic acid. The residue was triturated with IPE to provide Int-7 as a colorless solid (9.42 g, 59%). This material displayed spectral characteristics consistent with its assigned structure.

Preparation of I-3:

A mixture of 1,4,5,8-naphthalenetetracarboxylic acid dianhydride (0.67 g, 2.5 mmol) and Int-7 (1.42 g, 6.2 mmol), tri-n-butylamine (1.3 g, 7.0 mmol) and 10 ml of DMAc were combined then sealed in a pressure vessel. The mixture was heated at 135-140° C. for 1 hour then cooled. The resulting slurry was diluted with methanol and the solid filtered. The solid was washed with methanol and air dried to provide a peach solid. This solid was recrystallized from 50 ml of DMAc to afford a pale yellow solid (1.05 g, 74%). This material displayed spectral characteristics consistent with its assigned structure.

Preparation of Compound I-4:

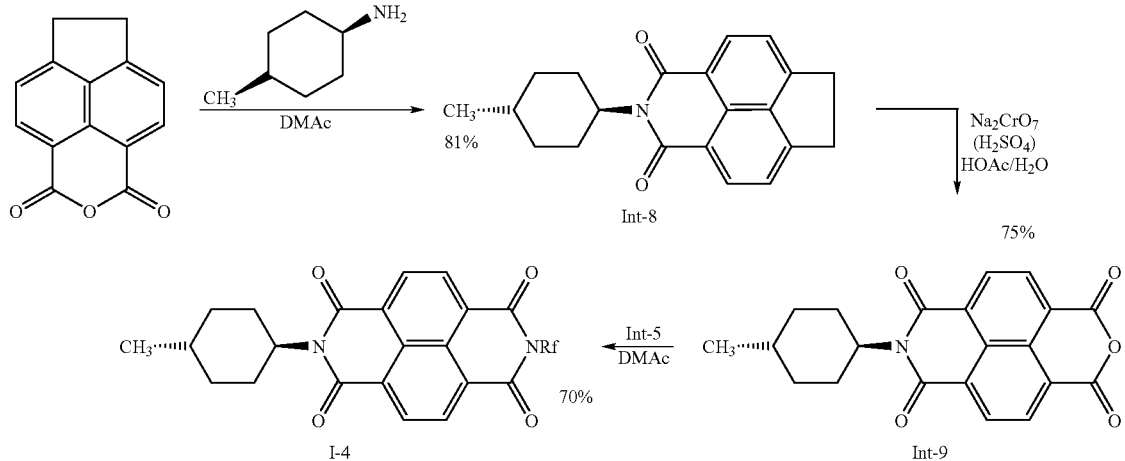

Preparation of Int-8:

A slurry of 5,6-acenaphthenedicarboxylic acid anhydride (CAS5699-00-3, 11.2 g, 50.0 mmol) in 50 ml of DMAc was treated with trans-4-methylcyclohexylamine (CAS 2523-55-9; 6.78 g, 60.0 mmol) and sealed in a pressure vessel. The mixture stirred at ambient temperature for 10 minutes and then was heated at 155-160° C. for 2 hours. The resulting dark solution was poured into 750 ml of water. The mixture was stirred for 10 min and then filtered. The accumulated solid was washed with water and air-dried to provide a dark solid (15.7 g, 98.4%). This solid was dissolved in 1 liter of dichloromethane (DCM), and then passed through silica gel (slurry-packed 25 cm×6 cm column) by eluting with 2 liters of DCM. The eluent was concentrated in vacuo to provide a solid. This solid was heated to reflux in a mixture of isopropyl ether and heptanes (200 ml; 1:1 v/v), and then allowed to cool to ambient temperature and then the solid was isolated via filtration and air drying: yellow solid (15.0 g, 94%). This material displayed spectral characteristics consistent with its assigned structure.

Preparation of Int-9:

A well-stirred solution of 200 ml of acetic acid and 20 ml of water was warmed to 95-100° C. (internal) and treated with sodium dichromate dihydrate (34.2 g, 0.115 mol). With the addition the mixture temperature fell. When the internal temperature was warmed to 95-100° C., N-(trans-4-methylcyclohexyl)-5,6-acenaphthenedicarboxylic acid imide (8.80 g, 27.6 mmol) was added at once. A vigorous reaction ensued with reaction reflux initiating. The mixture was stirred at reflux for 5 hours, after which, the mixture, was cooled briefly. The warm mixture was poured onto ice and stirred. The cold mixture was filtered; the isolated solid was washed with water until the filtrate appeared colorless. The solid was air dried to provide a glassy solid (8.56 g, 85.5%). This material displayed spectral characteristics consistent with its assigned structure.

Preparation of I-4:

A mixture of N-(trans-4-methylcyclohexyl)-1,4,5,8-naphthalenetetracarboxylic acid anhydride imide (0.91 g, 2.5 mmol) and Int-5 (0.50 g, 3.0 mmol), and 10 ml of DMAc were combined then sealed in a pressure vessel, and heated at 135-140° C. for 1 hour, then cooled. The resulting slurry was diluted with methanol and the solid filtered. The solid was washed with methanol then air dried to provide a silver gray solid. This crude solid was recrystallized from 80 ml of xylenes to provide a pale yellow solid (0.54 g, 42%). This material displayed spectral characteristics consistent with its assigned structure.

Preparation of Compound I-8:

A slurry of naphthalene 1,4,5,8-tetracarboxylic acid dianhydride (CAS 81-30-1, 0.67 g, 2.5 mmol) in 10 ml of N,N-dimethylacetamide (DMAc) was treated with trans-4-(nonafluorobutyl)-cyclohexylamine [prepared from 4-nonafluorophenol (CAS123068-23-5) as outlined above for trans-4-trifluoromethycyclohexylamine, Int-5, 2.5 g, 7.6 mmol]. The mixture was sealed in a pressure vessel then heated at 135-140° C. for 1 hour, and then cooled. The resulting slurry poured into water and filtered. The isolated solid was washed with water and air-dried. This solid was recrystallized from 100 ml of xylenes to give I-8 as a peach solid (1.72 g, 77%). This material displayed spectral characteristics consistent with its assigned structure.

Preparation of Compound I-7:

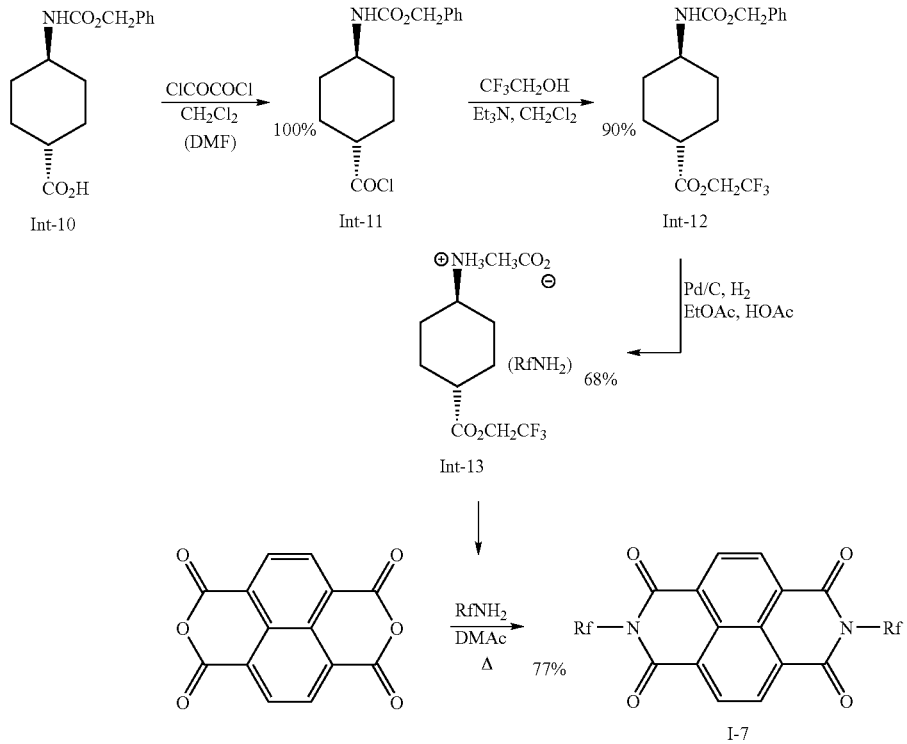

Preparation of Int-11:

A mixture of Int-10 (CAS 34771-04-5; 5.4 g, 18 mmol) in 125 ml of methylene chloride was treated with oxalyl chloride (CAS 79-37-8, 3.8 g, 30 mmol) then one drop of N,N-dimethylformamide (DMF), and vigorous gas evolution ensued. As gas evolution slowed, a second drop of DMF was added. When gas evolution ceased, the mixture was concentrated in vacuo. Subsequently, portions of heptanes were flashed off to provide the crude acid chloride Int-11.

Preparation of Int-12:

A solution of crude Int-11 (18 mmol) in 120 ml of methylene chloride was sequentially treated with 2,2,2-trifluoroethyl alcohol (CAS 75-89-8, 1.5 ml, 20.5 mmol) and then triethylamine (3.6 ml, 27 mmol). The mixture was stirred at ambient temperature for 2.5 hours then was diluted with saturated aqueous boric acid. The organics were separated, dried, and then concentrated in vacuo, to afford Int-12 (6.3 g, 90%). This material displayed spectral characteristics consistent with its assigned structure.

Preparation of Int-13:

A solution of Int-12 (6.0 g, 16.7 mmol) in 150 ml of ethyl acetate with 2 ml of acetic acid was treated with 10% Pd/C (ca. 100 mg) and then shaken at ambient temperature on a Parr® apparatus under hydrogen pressure ($P_0$=50 psi) for 6.5 hours. The mixture was filtered to remove the catalyst and the filtrate was concentrated in vacuo to a glassy oil. This material was stirred in IPE containing a small amount of acetic acid, to provide Int-13 as a colorless solid (3.2 g, 68%). This material displayed spectral characteristics consistent with its assigned structure.

Preparation of I-7:

A mixture of 1,4,5,8-naphthalenetetracarboxylic acid dianhydride (1.4 g, 5.2 mmol) and Int-13 (3.0 g, 10.5 mmol), tri-n-butylamine (2.6 ml, 10.9 mmol) and 9 ml of DMAc were combined then sealed in a pressure vessel. The mixture was heated at 135-140° C. for 40 minutes and then cooled. The resulting slurry was diluted with methanol and the solid filtered. The solid was washed with methanol and air dried to provide a off-white solid (2.79 g, 77%). This material displayed spectral characteristics consistent with its assigned structure.

Compound C-1 was prepared from commercially available 2,2,3,3,4,4,4-heptafluorobutylamine as follows.

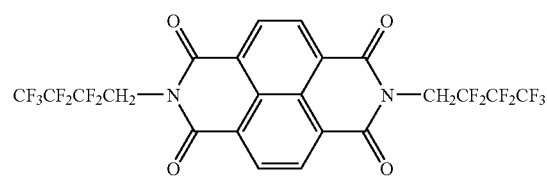

C-1

Preparation of Compound C-1:

A slurry of naphthalene 1,4,5,8-tetracarboxylic acid dianhydride (CAS 81-30-1; 0.41 g, 1.5 mmol) in 10 ml of DMAc was treated with 2,2,3,3,4,4,4-heptafluorobutylamine (CAS 377-99-2, 0.69 g, 3.5 mmol). The homogenous mixture was sealed in a pressure vessel then heated at 135-140° C. for 1 hour, and then cooled. The resulting slurry was diluted with several volumes of methanol and filtered. The isolated solid was washed with methanol and air-dried to provide C-1 as an orange solid. This solid was recrystallized from 50 ml of 1-butanol to give C-1 as a yellow solid (0.54 g, 56%). This material displayed spectral characteristics consistent with its assigned structure.

All compounds of the invention were purified by train sublimation at $10^{-5}$ to $10^{-6}$ torr.

Device Preparation:

In order to test the electrical characteristics of the various materials of this invention, field-effect transistors were typically made using the top-contact geometry. The substrate used is a heavily doped silicon wafer, which also serves as the gate of the transistor. The gate dielectric is a thermally grown $SiO_2$ layer with a thickness of 185 nm. It has been previously shown for both p-type and n-type transistors that electrical properties can be improved by treating the surface of the gate dielectric. For most of the experiments described here, the oxide surface was treated with a thin (<10 nm), spin-coated polymer layer, or a self-assembled monolayer (SAM) of octadecyltrichlorosilane (OTS). Typically, an untreated oxide sample was included in the experiments for comparison.

The active layer of naphthalene tetracarboxylic acid diimide was deposited via vacuum deposition in a thermal evaporator. The deposition rate was 0.1 Angstroms per second while the substrate temperature was held at 20° C. for most experiments. The thickness of the active layer was a variable in some experiments, but was typically 17-25 nm. Gold contacts of thickness 50-60 nm were deposited through a shadow mask. The channel width was held at 600 μm, while the channel lengths were either 50, 100, or 150 μm. Some experiments were performed to look at the effect of other contact materials. A few devices were made with a bottom-contact geometry, in which the contacts were deposited prior to the active material.

Device Measurement and Analysis:

Electrical characterization of the fabricated devices was performed with a Hewlett Packard HP 4145b® parameter analyzer. The probe measurement station was held in a positive argon environment for all measurements with the exception of those purposely testing the stability of the devices in air. The measurements were performed under sodium lighting unless sensitivity to white light was being investigated. The devices were exposed to air prior to testing.

For each experiment performed, between 4 and 12 individual devices were tested on each sample prepared, and the results were averaged. For each device, the drain current (Id) was measured as a function of source-drain voltage ($V_d$) for various values of gate voltage ($V_g$). For most devices, $V_d$ was swept from 0 V to 100 V for each of the gate voltages measured, typically 25 V, 50V, 75 V, and 100 V. In these measurements, the gate current ($I_g$) was also recorded in order to detect any leakage current through the device. Furthermore, for each device the drain current was measured as a function of gate voltage for various values of source-drain voltage. For most devices, Vg was swept from 0 V to 100 V for each of the drain voltages measured, typically 25 V, 50 V, 75 V, and 100 V.

Parameters extracted from the data include field-effect mobility (μ), threshold voltage (Vth), subthreshold slope (S), and the ratio of Ion/Ioff for the measured drain current. The field-effect mobility was extracted in the saturation region, where $V_d > V_g - V_{th}$. In this region, the drain current is given by the equation (see Sze in *Semiconductor Devices—Physics and Technology*, John Wiley & Sons (1981)):

$$I_d = \frac{W}{2L}\mu C_{ox}(V_g - V_{th})^2$$

Where, W and L are the channel width and length, respectively, and $C_{ox}$ is the capacitance of the oxide layer, which is a function of oxide thickness and dielectric constant of the material. Given this equation, the saturation field-effect mobility was extracted from a straight-line fit to the linear portion of the $\sqrt{I_d}$ versus $V_g$ curve. The threshold voltage, $V_{th}$, is the x-intercept of this straight-line fit. Mobilities can also be extracted from the linear region, where $V_d \leq V_g - V_{th}$. Here the drain current is given by the equation (see Sze in *Semiconductor Devices—Physics and Technology*, John Wiley & Sons (1981)):

$$I_d = \frac{W}{L}\mu C_{ox}\left[V_d(V_g - V_{th}) - \frac{V_d^2}{2}\right]$$

For these experiments, mobilities in the linear regime were not extracted, since this parameter is very much affected by any injection problems at the contacts. In general, non-linearities in the curves of $I_d$ versus $V_d$ at low $V_d$ indicate that the performance of the device is limited by injection of charge by the contacts. In order to obtain results that are largely independent of contact imperfections of a given device, the saturation mobility rather than the linear mobility was extracted as the characteristic parameter of device performance.

The log of the drain current as a function of gate voltage was plotted. Parameters extracted from the log $I_d$ plot include the $I_{on}/I_{off}$ ratio and the sub-threshold slope (S). The $I_{on}/I_{off}$ ratio is simply the ratio of the maximum to minimum drain current, and S is the inverse of the slope of the $I_d$ curve in the region over which the drain current is increasing (i.e. the device is turning on).

Results:

The following examples demonstrate that control over conformation of substituents in cyclohexane rings in N—N'-disubstituted-1,4,5,8-naphthalene tetracarboxylic acid diimides provides significantly improved electrical performance in n-channel semiconductor OTFT devices.

Comparative Example 1

This example demonstrates the n-type TFT device made from an linear fluorinated alkyl chain containing N,N'-(1H, 1H-perfluorobutyl)-1,4,5,8-naphthalene tetracarboxylic acid diimide C-1 on an OTS modified $SiO_2$ dielectric.

A heavily doped silicon wafer with a thermally-grown $SiO_2$ layer with a thickness of 185 nm was used as the substrate. The wafer was cleaned for 10 minutes in a piranha solution, followed by a 6-minute exposure in an UV/ozone chamber. The cleaned surface was then treated with a self-assembled monolayer of octadecyltrichlorosilane (OTS), made from a heptane solution under a humidity-controlled environment. Water contact angles and layer thicknesses were measured to ensure the quality of the treated surface. Surfaces with a good quality OTS layer have water contact angles >90°, and a thickness determined from ellipsometry in the range of 27 Å to 35 Å.

The devices were exposed to air prior to measurement in an argon atmosphere using a Hewlett-Packard® 4145B semiconductor parameter analyzer. For each transistor, the field effect mobility, μ, was calculated from the slope of the $(I_D)^{1/2}$ versus $V_G$ plot. The average mobility was found to be 0.33 $cm^2/Vs$ in the saturation region. The average on-off ratio was $1.3 \times 10^7$, and the average threshold voltage was 39.17V. Saturation mobilities of up to 0.4 $cm^2/Vs$ were measured for devices prepared in this way.

Invention Example 1

The purified configurationally controlled N,N'-(trans-4-trifluoromethylcyclohexyl)-1,4,5,8-naphthalene tetracarboxylic acid diimide I-2 was deposited by vacuum sublimation at a pressure of $2 \times 10^{-7}$ Torr and a rate of 0.1 Angstroms per second to a thickness of 17-20 nm as measured by a quartz crystal. During deposition the substrate was held at room temperature of 20° C. The sample was exposed to air for a short time prior to subsequent deposition of Au source and drain electrodes through a shadow mask to a thickness of 50-60 nm. The devices made had a 600 μm channel width, with channel lengths varying from 50 to 150 μm. Multiple OTFTs were prepared and representative samples of 4 to 8 OTFTs were tested for each deposition run. Devices were tested both under argon (Ar) and in air. The averaged results appear in TABLE I below.

TABLE I

| | Active OTFT Material | Test Conditions | μ ($cm^2/Vs$) | σ (μ) | $V_{th}$ (V) | σ ($V_{th}$) | $I_{on}I_{off}$ |
|---|---|---|---|---|---|---|---|
| Comparative Example 1 | C-1 | Under argon | 0.33 | 0.04 | 39.17 | 3.55 | $1.34 \times 10^7$ |
| | | Air | 0.35 | 0.02 | 63.3 | 3.54 | $2.57 \times 10^7$ |
| Inventive Example 1 | I-2 | Under argon | 0.49 | 0.01 | 17.75 | 0.46 | $1.05 \times 10^7$ |
| | | Air | 0.37 | 0.02 | 17.49 | 1.6 | $7.78 \times 10^6$ |

Comparative Example 1 and Invention Example 1 clearly demonstrate the advantage of using Compound I-2 as n-type material in a thin film transistor. The mobility and $V_{th}$ for Invention Example 1 were both are improved over the results with Comparative Example 1 thereby demonstrating the advantageous effect on device performance from use of the fluoroalkyl group substituted cyclohexane ring compared to use of the device with the linear fluorinated alkyl group. The advantage of the inventive material was especially evident when the devices are tested in air, showing improved stability.

Comparative Example 2

A heavily doped silicon wafer with a thermally-grown $SiO_2$ layer with a thickness of 185 nm was used as the substrate. The wafer was cleaned for 10 minutes in a piranha solution, followed by a 6-minute exposure in a UV/ozone chamber. The purified C-1 was deposited by vacuum sublimation at a pressure of $2 \times 10^{-7}$ Torr and a rate of 0.1 Angstroms per second to a thickness of 17-20 nm as measured by a quartz crystal. During deposition the substrate was held at room temperature of 20° C. The sample was exposed to air for a short time prior to subsequent deposition of Au source and drain electrodes through a shadow mask to a thickness of 50 nm. The devices made had a 600 μm channel width, with channel lengths varying from 50 to 150 μm. Multiple OTFT's were prepared and representative samples of 4 to 8 OTFT's were tested for each deposition run. Devices were tested both under argon (Ar) and in air. The averaged results appear in TABLE II below.

Invention Example 2

A heavily doped silicon wafer with a thermally-grown $SiO_2$ layer with a thickness of 185 nm was used as the substrate. The wafer was cleaned for 10 minutes in a piranha solution, followed by a 6-minute exposure in a UV/ozone chamber. The purified I-2 was deposited by vacuum sublimation at a pressure of $2 \times 10^{-7}$ Torr and a rate of 0.1 Angstroms per second to a thickness of 17-20 nm as measured by a quartz crystal. During deposition the substrate was held at room temperature of 20° C. The sample was exposed to air for a short time prior to subsequent deposition of Au source and drain electrodes through a shadow mask to a thickness of 50 nm. The devices made had a 600 μm channel width, with channel lengths varying from 50 to 150 μm. Multiple OTFT's were prepared and representative samples of 4 to 8 OTFT's were tested for each deposition run. Devices were tested in air. The averaged results appear in TABLE II below.

Comparative Example 2 and Inventive Example 2 clearly demonstrate the advantage of using Compound I-2 as n-type material on a $SiO_2$ dielectric in a thin film transistor. The mobility and $V_{th}$ of the invention device were both improved over the device for Comparative Example 2 demonstrating the advantageous effect on device performance containing the fluoroalkyl group substituted cyclohexane ring over the device containing the linear fluorinated alkyl group.

Invention Example 3

This example demonstrates the improved performance of an n-type TFT device using N,N'-(cis-4-trifluoromethylcyclohexyl)-1,4,5,8-naphthalene tetracarboxylic acid diimide (Compound I-3) in accordance with the present invention. An n-type OTFT device comprising Compound I-3 as the active material was made as described earlier in Invention Example 1. The averaged results appear in TABLE III below.

TABLE III

| | Active OTFT Material | Test Conditions | μ (cm²/Vs) | σ (μ) | $V_{th}$ (V) | σ ($V_{th}$) | $I_{on}I_{off}$ |
|---|---|---|---|---|---|---|---|
| Comparative Example 1 | C-1 | Under Ar | 0.33 | 0.04 | 39.17 | 3.55 | $1.34 \times 10^7$ |
| | | Air | 0.35 | 0.02 | 63.3 | 3.54 | $2.57 \times 10^7$ |
| Inventive Example 3 | I-3 | Under Ar | 0.19 | 0.01 | 20.43 | 3.67 | $3.44 \times 10^7$ |
| | | Air | 0.20 | 0.03 | 20.21 | 1.62 | $7.55 \times 10^6$ |

Comparative Example 1 and Invention Example 3 clearly demonstrate the advantage of using Compound I-3 as n-type material in a thin film transistor. The $V_{th}$ position of the invention device was improved over Comparative Example 1 demonstrating the advantageous effect on device performance of fluoroalkyl group substituted cyclohexane ring over the device with the linear fluorinated alkyl group. The advantage of the invention device was especially evident when the devices were tested in air.

Invention Example 4

This example demonstrates the improved performance of an n-type TFT device using N-(trans-4methylcyclohexyl)-N'-(cis-4-trifluoromethylcyclohexyl)-1,4,5,8-naphthalene tetracarboxylic acid diimide (Compound I-4) in accordance with the present invention. An n-type TFT device comprising Compound I-4 as the active material was made as described above in Invention Example 1. The averaged results appear in TABLE IV below.

TABLE II

| | Active OTFT Material | Test Conditions | μ (cm²/Vs) | σ (μ) | $V_{th}$ (V) | σ ($V_{th}$) | $I_{on}I_{off}$ |
|---|---|---|---|---|---|---|---|
| Comparative Example 2 | C-1 | Air | $7 \times 10^{-3}$ | $10^{-4}$ | 69.9 | 2.57 | $5.25 \times 10^4$ |
| Inventive Example 2 | I-2 | Air | 0.21 | 0.01 | 25.39 | 1.61 | $4.34 \times 10^6$ |

TABLE IV

| | Active OTFT Material | Test Conditions | μ (cm²/Vs) | σ (μ) | $V_{th}$ (V) | σ ($V_{th}$) | $I_{on}I_{off}$ |
|---|---|---|---|---|---|---|---|
| Comparative Example 1 | C-1 | Under argon | 0.33 | 0.04 | 39.17 | 3.55 | $1.34 \times 10^7$ |
| | | Air | 0.35 | 0.02 | 63.3 | 3.54 | $2.57 \times 10^7$ |
| Inventive Example 4 | I-4 | Under argon | 0.87 | 0.045 | 27.9 | 1.9 | $2.84 \times 10^7$ |
| | | Air | 0.87 | 0.06 | 18.3 | 1.6 | $4.7 \times 10^7$ |

Comparative Example 1 and Inventive Example 4 clearly demonstrate the advantage of using Compound I-4 as n-type material in a thin film transistor. The mobility and $V_{th}$ for the inventive device were both improved over that for the device of Comparative Example 1 demonstrating the advantageous effect on device performance of fluoroalkyl group substituted cyclohexane ring over the device with the linear fluorinated alkyl group. The advantage of the inventive device was especially evident when the devices were tested in air.

Invention Example 5

This example demonstrates the improved performance of an n-type TFT device using N,N'-(trans-4-perfluorobutylcyclohexyl)-1,4,5,8-naphthalene tetracarboxylic acid diimide (Compound I-7) in accordance with the present invention. An n-type TFT device comprising Compound I-7 as the active material was made as described earlier in Invention Example 1. The averaged results appear in TABLE V below.

TABLE V

| | Active OTFT Material | Test Conditions | μ (cm²/Vs) | σ (μ) | $V_{th}$ (V) | σ ($V_{th}$) | $I_{on}I_{off}$ |
|---|---|---|---|---|---|---|---|
| Comparative Example 1 | C-1 | Under argon | 0.33 | 0.04 | 39.17 | 3.55 | $1.34 \times 10^7$ |
| | | Air | 0.35 | 0.02 | 63.3 | 3.54 | $2.57 \times 10^7$ |
| Inventive Example 5 | I-7 | Under argon | 0.37 | 0.04 | 17.8 | 3.0 | $5.4 \times 10^7$ |
| | | Air | 0.39 | 0.05 | 17.3 | 2.9 | $1.5 \times 10^7$ |

Comparative Example 1 and Inventive Example 5 clearly demonstrate the advantage of using Compound I-7 as n-type material in a thin film transistor. The mobilities are comparable for the two devices but the $V_{th}$ of the inventive device was significantly better than that for the device of Comparative Example 1. These results clearly demonstrate the advantageous effect of having a fluoroalkyl group substituted cyclohexane ring compared to having a linear fluoroalkyl group. The $V_{th}$ advantage of the inventive device was especially evident when the devices were tested in air.

Invention Example 6

This example demonstrates the improved performance of an n-type TFT device using Compound I-8 in accordance with the present invention. An n-type TFT device comprising Compound I-7 as the active material was made as described earlier in Invention Example 1. The averaged results appear in TABLE VI below.

TABLE VI

| | Active OTFT Material | Test Conditions | μ (cm²/Vs) | σ (μ) | $V_{th}$ (V) | σ ($V_{th}$) | $I_{on}I_{off}$ |
|---|---|---|---|---|---|---|---|
| Comparative Example 1 | C-1 | Under argon | 0.33 | 0.04 | 39.17 | 3.55 | $1.34 \times 10^7$ |
| | | Air | 0.35 | 0.02 | 63.3 | 3.54 | $2.57 \times 10^7$ |
| Inventive Example 6 | I-8 | Under argon | 0.21 | 0.03 | 27.9 | 4.2 | $4.3 \times 10^6$ |
| | | Air | 0.25 | 0.05 | 25.3 | 4.0 | $2.0 \times 10^6$ |

Comparative Example 1 and Inventive Example 6 clearly demonstrate the advantage of using Compound I-8 as n-type material in a thin film transistor. The mobilities of the devices were comparable but the $V_{th}$ of the inventive device was significantly better than the device of Comparative Example 1. This clearly demonstrates the advantageous effect of having device with a fluoroalkyl group substituted cyclohexane ring compared to a device having a linear fluoroalkyl group. The $V_{th}$ advantage of the inventive device was especially evident when the devices were tested in air.

PARTS LIST 20 source electrode
28 substrate
30 drain electrode
44 gate electrode
56 gate dielectric
70 semiconductor

The invention claimed is:

1. An article comprising, in a thin film transistor, a thin film of organic semiconductor material that comprises an N,N'-1,4,5,8-naphthalenetetracarboxylic acid diimide that is represented by the following Structure I:

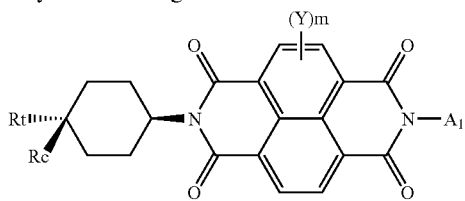

(I)

wherein $R_c$ represents a fluorinated substituent in the C-4 cis configuration with respect to the imide group, and $R_t$ represents a fluorinated substituent in the C-4 trans configuration with respect to the imide group, and one of $R_c$ and $R_t$ can be hydrogen, $A_1$ is a substituted or unsubstituted cycloalkyl group, Y represents an alkyl and m is 0.

2. The article of claim 1 wherein $A_1$ is the same or different fluorinated substituent as $R_c$.

3. The article of claim 1 wherein said fluorinated substituent is a saturated fluoroalkyl group having 1 to 5 carbon atoms.

4. The article of claim 1 wherein said thin film of organic semiconductor material comprises a N,N'-fluorinated dicycloalkyl-substituted-1,4,5,8-naphthalene tetracarboxylic acid diimide compound represented by the following Structure II(a) or (b):

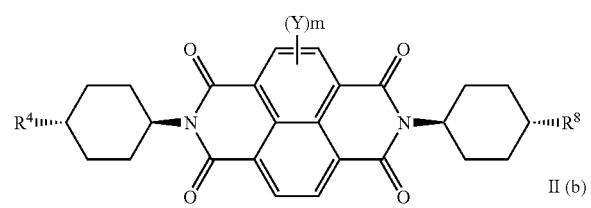

II (a)

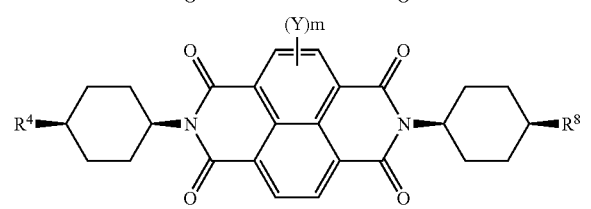

II (b)

wherein $R^4$ is a fluorinated organic substituent, and $R^8$ independently hydrogen or a fluorinated substituent, wherein each of $R^4$ and, if substituted, $R^8$ are either one, but only one, of an essentially trans or cis configuration with respect to the attachment to the imine nitrogen.

5. The article of claim 4 wherein both $R^4$ and $R^8$ are the same or different saturated fluoroalkyl groups having 1 to 5 carbon atoms or the same or different esters having saturated fluoroalkyl groups having 1 to 5 carbon atoms.

6. The article of claim 4 wherein both $R^4$ and $R^8$ are the same saturated fluoroalkyl groups having 1 to 4 carbon atoms.

7. The article of claim 1 wherein the thin film transistor is a field effect transistor comprising a dielectric layer, a gate electrode, a source electrode and a drain electrode, and wherein the dielectric layer, the gate electrode, the thin film of organic semiconductor material, the source electrode, and the drain electrode are in any sequence as long as the gate electrode and the thin film of organic semiconductor material both contact the dielectric layer, and the source electrode and the drain electrode both contact the thin film of organic semiconductor material.

8. The article of claim 1 wherein the thin film of organic semiconductor material is capable of exhibiting electron mobility greater than 0.001 cm$^2$/Vs.

9. The article of claim 1 wherein the thin film transistor has an on/off ratio of a source/drain current of at least 10$^4$.

10. The article of claim 7 wherein the gate electrode is adapted for controlling, by means of a voltage applied to the gate electrode, a current between the source and drain electrodes through the thin film of organic semiconductor material.

11. The article of claim 7 wherein the dielectric layer comprises an inorganic or organic electrically insulating material.

12. The article of claim 7 wherein the source, drain, and gate electrodes each independently comprise a material selected from doped silicon, metal, and a conducting polymer.

13. The article of claim 1 wherein the thin film transistor further comprises a non-participating support that is optionally flexible.

14. An electronic device that is an integrated circuit, active-matrix display, or solar cell that comprises a multiplicity of the thin film transistors of claim 1.

15. The electronic device of claim 14 wherein the multiplicity of the thin film transistors is on a non-participating support that is optionally flexible.

16. A process for fabricating a thin film semiconductor device, comprising, not necessarily in the following order, the steps of:

(a) depositing, onto a substrate, a thin film of n-channel organic semiconductor material that comprises an N,N'-1,4,5,8-naphthalenetetracarboxylic acid diimide having at least one cycloalkyl group that has a fluorinated substituent containing at least one fluorine at its 4-position, such that the organic semiconductor material exhibits a field effect electron mobility that is greater than 0.001 cm$^2$/Vs, (b) forming a spaced apart source electrode and drain electrode,
wherein the source electrode and the drain electrode are separated by, and electrically connected with, the n-channel semiconductor film, and (c) forming a gate electrode spaced apart from the organic semiconductor material,
wherein said N,N'-1,4,5,8-naphthalenetetracarboxylic acid diimide is represented by the following Structure I:

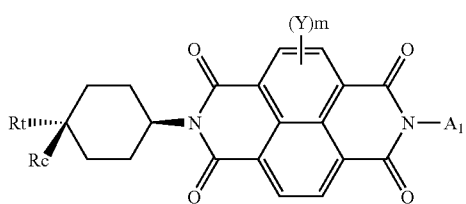

wherein $R_c$ represents a fluorinated substituent in the C-4 cis configuration with respect to the imide group, and $R_t$ represents a fluorinated substituent in the C-4 trans configuration with respect to the imide group, and one of $R_c$ and $R_t$ can be hydrogen, $A_1$ is a substituted or unsubstituted cycloalkyl group, Y represents an alkyl and m is 0.

17. The process of claim 16 wherein said thin film is deposited on the substrate by sublimation and wherein the substrate has a temperature of no more than 100° C. during deposition.

18. The process of claim 16, wherein said thin film comprises one or more of the following compounds I-1 through I-9:

I-1 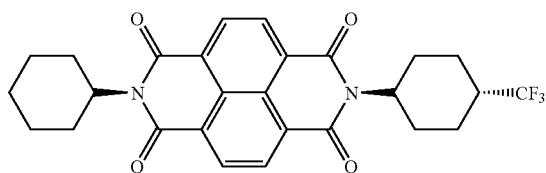

I-2 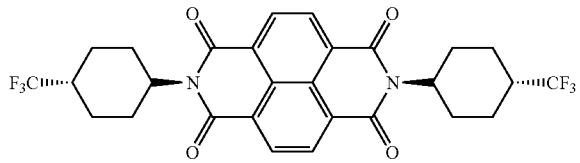

I-3 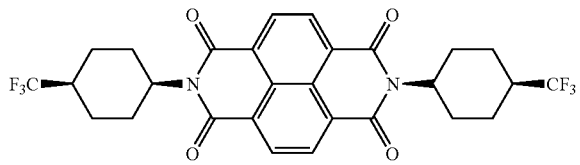

I-4 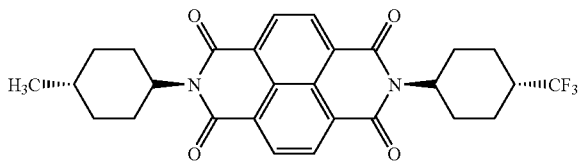

I-5 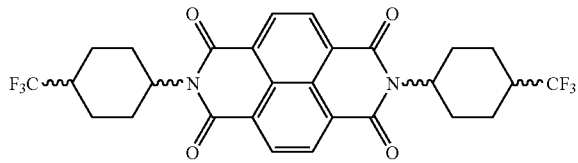

I-6 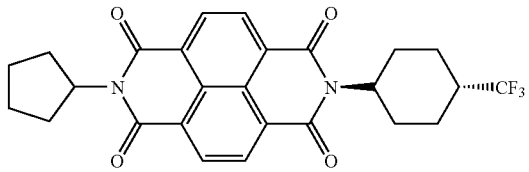

I-7 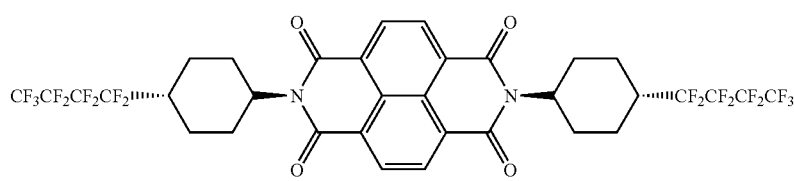

-continued
I-8
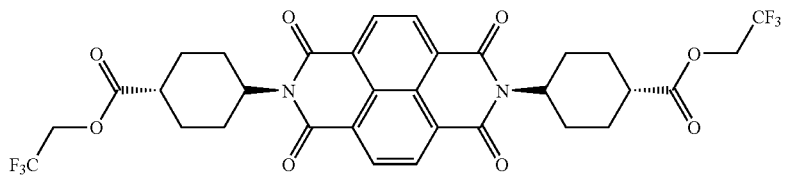
I-9
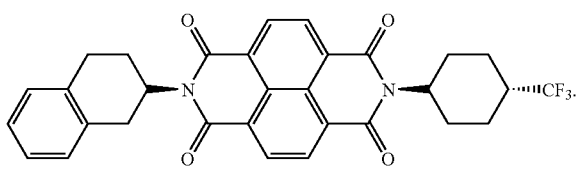
* * * * *